United States Patent
Aven et al.

(10) Patent No.: US 7,176,209 B2
(45) Date of Patent: Feb. 13, 2007

(54) FUNGICIDAL FORMULATION

(75) Inventors: Michael Aven, Mainz (DE); Ewald Sieverding, St. Johann Rheinhess (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/362,058

(22) PCT Filed: Aug. 24, 2001

(86) PCT No.: PCT/EP01/09786

§ 371 (c)(1),
(2), (4) Date: Feb. 20, 2003

(87) PCT Pub. No.: WO02/15697

PCT Pub. Date: Feb. 28, 2002

(65) Prior Publication Data

US 2003/0176427 A1 Sep. 18, 2003

Related U.S. Application Data

(60) Provisional application No. 60/228,328, filed on Aug. 25, 2000.

(51) Int. Cl.
*A01N 43/90* (2006.01)
*A01N 43/54* (2006.01)
(52) U.S. Cl. .............. 514/259.31; 514/222.2; 514/228.8; 514/241; 514/247; 514/772.3
(58) Field of Classification Search ........ 514/258, 514/937, 975, 259.31, 222.2, 228.8, 241, 514/247, 772.3
See application file for complete search history.

(56) References Cited

U.S. PATENT DOCUMENTS

| 4,880,620 A | * | 11/1989 | Vanlerberghe et al. ... 424/70.21 |
| 5,558,684 A | * | 9/1996 | DeRosa et al. ........... 44/419 |
| 6,124,301 A | * | 9/2000 | Aven et al. ........... 514/259.31 |
| 6,656,883 B1 | * | 12/2003 | Vogt et al. ........... 504/105 |

FOREIGN PATENT DOCUMENTS

| EP | 550 113 | 7/1993 |
| EP | 943 241 | 9/1999 |
| WO | 00/18227 | 4/2000 |

* cited by examiner

*Primary Examiner*—John Pak
(74) *Attorney, Agent, or Firm*—Novak Druce & Quigg LLP

(57) ABSTRACT

Adjuvants selectes from mon/ionic water/soluble mixed polyalkoxy-lated aliphatic alcohol surfactants, non ionic water soluble ethoxylated aliphatic alcohol surfactants, amine ethoxylates, and micronized polymeric waxes enhance the efficacy of fungicidal triazolopzrimidines of structural formula I. They can be incorporated into formulations of the fungicidal compounds or be added to spray mixtures (tank mix) as separately formualted additives in order to improve the efficacy and spectrum of these fungicides. This invention also provides fungicidal compositions of said triazolopzrimidines and adjuvants, as well as methods for their use in the control of photopathogenic fungi

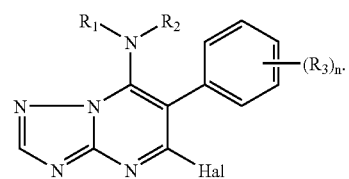

9 Claims, No Drawings

FUNGICIDAL FORMULATION

This application is a 371 of PCT/EP01/09786, filed on Aug. 24, 2001, which claims benefit of U.S. Provisional Application No. 60/228,328, filed on Aug. 25, 2000.

DESCRIPTION

As a rule, inert carrier ingredients must be used to bring crop protection agents, for example, fungicidal compounds, into a form that the user can apply them either as such, or after dilution with water. The choice of formulation type and inert ingredients for that formulation type often determines to a significant extent whether the active ingredient can display its full activity on application.

The efficacy of the active components can often be improved by addition of other (active) ingredients. The observed efficacy of the combination of ingredients can sometimes be significantly higher than that would be expected from the amounts of the individual ingredients used, thus indicating synergism from the components of the combination.

The usual components of formulations such as carriers and inert ingredient (e.g. organic solvents, suspension agents, emulsion agents, wetting agents, solubilizing agents) which do not themselves possess pesticidal activity, however, do not usually lead to an unexpected increase in efficacy.

International Patent Application WO 95/01722 discloses pesticidal formulations containing non-ionic surface-active agents which can be selected, inter alia, from liquid polyalkoxylated aliphatic alcohols. However, the addition of these agents is directed to improving the storage stability of the formulations, and there is no report of enhancing the activity of fungicides used in the formulations.

U.S. Pat. No. 4,851,421 discloses the use of polyalkylene-type non-ionic surface active agents derived from the alkoxylation of fatty alcohols with alkyleneoxides, polyoxyalkylene mono- or dialkylphenyether or polyoxyalkylene sorbitan fatty acid esters.

It is an object of this invention to provide methods for further enhancement of the efficacy of said fungicidal triazolopyrimidines. It is another object of this invention to provide fungicidal compositions of said triazolopyrimidines and adjuvants, as well as methods for their use in the control of phytopathogenic fungi.

There is ongoing research to identify suitable adjuvants which combination with the active fungicidal ingredient provide a means to lower the dose of active fungicidal agent required for effective disease control. This goal is desirable from both an economic and an environmental standpoint.

EP-A 71 792 and EP-A 550 113 disclose fungicidal triazolopyrimidine compounds. EP-A 943 241 describes the enhancement of the fungicidal efficacy of said triazolopyrimidines by the addition of selected adjuvants from the liquid polyalkoxylated aliphatic alcohol class.

It has now been found that the effective amounts of fungicidal triazolopyrimidines of formula I

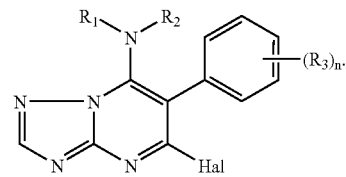

in which
R$^1$ and R$^2$ independently denote hydrogen or
  C$_1$–C$_{10}$-alkyl, C$_2$–C$_{10}$-alkenyl, C$_2$–C$_{10}$-alkynyl, or
  C$_4$–C$_{10}$-alkadienyl,
  C$_3$–C$_{10}$-cycloalkyl, phenyl, naphthyl, or
  5- or 6-membered heterocyclyl, containing one to four nitrogen atoms or one to three nitrogen atoms and one sulfur or oxygen atom, or
  5- or 6-membered heteroaryl, containing one to four nitrogen atoms or one to three nitrogen atoms and one sulfur or oxygen atom, or
  where R$^1$ and R$^2$ radicals may be unsubstituted or may carry one to three groups R$^a$,
R$^a$ is cyano, nitro, hydroxyl, C$_1$–C$_6$-alkyl, C$_1$–C$_6$-haloalkyl, C$_3$–C$_6$-cycloalkyl, C$_1$–C$_6$-alkoxy, C$_1$–C$_6$-haloalkoxy, C$_1$–C$_6$-alkylthio, C$_1$–C$_6$-alkylamino, di-C$_1$–C$_6$-alkylamino, C$_2$–C$_6$-alkenyl, C$_2$–C$_6$-alkenyloxy, C$_2$–C$_6$-alkynyl, C$_3$–C$_6$-alkynyloxy and C$_1$–C$_4$-alkylenedioxy; or
R$^1$ and R$^2$ together with the interjacent nitrogen atom represent a 5- or 6-membered heterocyclic ring, containing one to four nitrogen atoms or one to three nitrogen atoms and one sulfur or oxygen atom, which may be substituted by one to three R$^a$ radicals;
R$^3$ represents halogen or C$_1$–C$_6$-alkyl or C$_1$–C$_6$-alkoxy;
n represents an integer from 0 to 5; and
Hal represents halogen;

which must be applied can be lowered considerably with respect to the amounts usually employed to achieve the same fungicidal effect, if these fungicidal compounds or their formulations are applied in combination with one or more adjuvants selected from the groups consisting of
a) non-ionic water-soluble mixed polyalkoxylated aliphatic alcohol surfactants,
b) non-ionic water soluble ethoxylated aliphatic alcohol surfactants,
c) amine ethoxylates, and
d) micronized polymeric waxes.

The biological activity of the active ingredient of formula I can be increased by including any of these adjuvants in the spray dilution or directly in the formulation. An adjuvant is defined here as a substance which can increase the biological activity of an active ingredient but is not itself significantly biologically active. The adjuvant can either be included in the formulation or can be added to the spray tank together with the formulation containing the active ingredient. The water-soluble mixed polyalkoxylated or ethoxylated aliphatic alcohols are particularly useful for liquid formulations, in particular for aqueous suspension concentrates (SC). The mixed polyalkoxylated adjuvants are containable by alkoxylation of fatty alcohols having 8–18 C-atoms, with alkylene oxides having 2–6, preferably with a mixture of ethylene oxide and propylene oxide. The aliphatic moieties of the said fatty alcohols may be straight-chained or branched. The ethoxy to propoxy ratio is from 50:50 to 90:10. Preferred water soluble non-ionic surfactants of the mixed alkoxylated aliphatic alcohol class are mixed random or block oligomers of formula II

$$H_{2n+1}C_n-O-(CH_2CH_2O)_x(CH_2CH(CH_3)O)_yH \qquad (II)$$

wherein
n is an integer from 8 to 18;
x is an integer from 3 to 10; and
y is an integer from 1 to 3.

Of particular interest are those water soluble mixed polyalkoxylated aliphatic alcohols which are commercially available under the trademark Plurafac® LF (Tensid-Chemie, Köln/BASF AG, Ludwigshafen). In particular Plurafac® LF 300 has been proven to be especially advantageous.

The water soluble polyethoxylated adjuvants are obtainable in similar fashion and are straight chained or branched $C_{10-25}$ alcohols ethoxylated with 10 to 25 ethoxy groups. Particularly preferred is Lubrol® 17A17, commercially available from Uniqema, Everberg, Belgium.

The amine ethoxylate adjuvants are tertiary amine ethoxylates based on primary amines such as oleyl amine and tallow amine. Particularly preferred are those commercially available under the trademark Berol 381® and Berol 303® (Ethomeen® S22) from Akzo Nobel Surface chemistry, Sweden.

A particularly preferred micronized polymeric wax is a modified polyethylene wax commercially available under the trademark ®Ceridust 9615A from Clariant GmbH, Augsburg, Germany.

The enhancement in efficacy by addition of the said adjuvants can be observed for the fungicidal triazolopyrimidines of formula I, preferably, wherein $R^1$ and $R^2$ together with the adjacent nitrogen atom represent an optionally substituted 6-membered heterocyclic ring, or wherein $R^1$ represents a $C_{1-6}$-alkyl, a $C_{1-6}$-haloalkyl, in particular $C_{1-6}$-fluoroalkyl, or a $C_{3-8}$-cycloalkyl group and $R^2$ represents a hydrogen atom or a $C_{1-6}$-alkyl group and/or wherein

wherein $L_1$ represents a halogen atom, preferably fluorine or chlorine and $L_2$ and $L_3$ each independently represents a hydrogen atom or a halogen atom, preferably fluorine and/or wherein Hal represents a chlorine atom.

In a particularly preferred embodiment the triazolopyrimidine is 5-chloro-6-(2-chloro-6-fluorophenyl)-7-N-(4-methylpiperid-1-yl)-[1,2,4]triazolo[1,5-α]pyrimidine coded compound IA, and 5-choro-6-(2,4,6-trifluoro-phenyl)-7-(2,2,2,-trifluoro-1-methyl-amino)[1,2,4]triazolo[1,5-α]pyrimidine coded compound IB.

The adjuvants of the present invention can be included in the formulation or added in a suitable form with the preparation of the spray mix (tank mix). In this latter case, they are added preferably as a separate preparation with the other components such as a dispersing agent or an antifoam and, where desirable, with further adjuvants so as to ensure that they are homogenously dispersed in the spray mix.

The present invention also relates to fungicidal formulations with at least one compound of formula I, adjuvants and/or carrier substances characterized by their containing, in addition to the conventional adjuvants and carriers, one or more adjuvants selected form the group consisting of a) non ionic water-soluble mixed polyalkoxylated aliphatic alcohol surfactants, b) non-ionic water soluble ethoxylated aliphatic alcohol surfactants, c) amine ethoxylates, and d) micronized polymeric waxes.

The fungicidal compounds can be applied as normal commercial formulations with adjuvants according to the invention, and where desirable, with additional components such as antioxidants and emulsion agents.

The appropriate relative amounts of active ingredient and the watersoluble adjuvant lie, in accordance with the invention, between 100:75 and 100:100,000, preferably between 100:90 and 100:50,000 and, more preferably, between 100:125 and 100:5,000. In general and within certain limits, the fungicidal efficacy can be enhanced to a higher degree by the addition of larger amounts of the adjuvant.

In a preferred embodiment the adjuvant is added to the tank mix together with the triazolopyrimidine as a formulation.

The present invention also relates to a kit for the preparation of a spray mixture consisting of two separate containment:

1) a containment which comprises at least one fungicide of formula I and conventional inert ingredients and carriers;

2) a containment which comprises at least one adjuvant selected from the group consisting of a) non-ionic water-soluble mixed polyalkoxylated aliphatic alcohol surfactants, b) non-ionic water soluble ethoxylated aliphatic alcohol surfactants, c) amine ethoxylates, and d) micronized polymeric wax.

In a preferred embodiment said kit will consist of two bottles with dispensing means which allow the easy and correct addition of the active ingredient (1) and the adjuvant (2) to the tank mix.

Recommended doses for various applications are known for the fungicidal compounds of formula I where the efficacy can be enhanced in accordance with the invention. Addition of the adjuvants suggested here can (depending on the active ingredient, the adjuvant and their amounts) reduce the amount of active ingredient per hectare required in these recommendations by half or more, whereby it becomes possible to control additional diseases at reasonable doses.

In a preferred embodiment the adjuvants in combination with the fungicide of formula I are applied at rates of 40 to 4000 ml/ha, preferably 50 to 3000 ml/ha, in particular 60 to 2000 ml/ha.

An important advantage is the rapid onset and the high persistency of activity on use of the new additives. This enlarges the period for application of the fungicide and, hence, makes it more useful.

The fungicidal formulations according to the present invention can be used in combination with said additives prophylactically and curatively.

The adjuvants according to the invention, the compounds of formula I, and usual adjuvants and carriers can be processed to the preferably fluid or dispersible solid formulations known in the art, for example, as solutions, emulsions, wettable powders (WPs), suspension concentrates (SCs), emulsion concentrates (ECs), low volume or ultra low volume preparations and water dispersible granules (WGs).

The preparations usually contain fluid and/or solid carries or solubilizing agents such as organic solvents like ketones, alcohols, fluid aliphatic, or aromatic compounds, fine natural or synthetic silicates or carbonates. The preparations also usually contain ionic and/or non-ionic surfactants which function as emulsion, dispersing or wetting agents. Antifoam and antifreeze agents may also be added. Suitable adjuvant and carriers substances are described in the literature and well known to the persons skilled in the art.

A composition according to the invention preferably contains from 0.5% to 95% by weight (w/w) of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including material which is normally a gas but which has been compressed to form a liquid.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

Examples of formulations according to the invention are shown in the following formulations A and B:

Formulation A: Suspension Concentrate (SC)

| Component | Amount [g/l] | Ingredient |
|---|---|---|
| active ingredient | 200.0 | Compound TA |
| dispersant | 30.0 | Morwet ® D425[1] |
| dispersant | 15.0 | Pluronic ® PE 10500[2] |
| antifoam agent | 2.0 | Rhodorsil ® 426 R[3] |
| structure agent | 1.0 | Rhodopol ® 23[3] |
| preservative | 2.0 | Proxel ® GXL[4] |
| structure agent | 5.0 | Veegum T[5] |
| antifreeze agent | 40.0 | propylene glycol |
| water | to 1000 ml | |

[1]Witco Corporation, Houston, USA
[2]Tensid-Chemie, Köln/BASF AG, Ludwigshafen, Germany
[3]Rhodia GmbH, Frankfurt, Germany
[4]Zeneca GmbH, Frankfurt, Germany
[5]Vanderbilt, Norwalk, USA The SC formulation described above is mixed before application with water to give a spray mix with the desired concentration of active ingredient. A non-ionic surface-active agent selected from the water-soluble mixed polyalkoxylated aliphatic alcohol class, in particular Plurafac® LF300 (250 g/l), is added to the resulting tank mix.

Formulation B: Suspension Concentrate (SC)

| Component | Amount [g/l] | Ingredient |
|---|---|---|
| active ingredient | 200.0 | Compound IA |
| dispersant | 30.0 | Morwet ® D425[1] |
| dispersant | 15.0 | Pluronic ® PE 10500[2] |
| preservative | 2.0 | Proxel ® GXL[3] |
| antifoam agent | 5.0 | SAG 220[1] |
| structure agent | 0.8 | Rhodopol ® 23[4] |
| structure agent | 5.0 | Vegum Pro[5] |
| water | to 1000 ml | |

[1]Witco Corporation, Houston, USA
[2]Tensid-Chemie, Köln/BASF AG, Ludwigshafen, Germany
[3]Zeneca GmbH, Frankfurt, Germany
[4]Rhodia GmbH, Frankfurt, Germany
[5]Vanderbilt, Norwalk, USA The SC formulation described above is mixed before application with water to give a spray mix with the desired concentration of active ingredient. A non-ionic surface-active agent selected from the water-soluble mixed polyalkoxylated aliphatic alcohols, in particular Plurafac® LF 300 (150 g/l) and additionally a non-ionic surface-active agent selected from the water soluble polyethoxylated aliphatic alcohol class, in particular Lubrol 17A17 (150 g/l) is added to the resulting tank mix.

It is also an object of the invention to suggest a method for the control of phytopathogenic fungi, characterized by the use of the compounds of formula I, in particular formula IA in combination with one or more adjuvants selected from the groups consisting of a) non-ionic water-soluble mixed polyalkoxylated aliphatic alcohol surfactants, b) non-ionic water soluble ethoxylated aliphatic alcohol surfactants, c) amine ethoxylates, and d) micronized polymeric waxes.

Plant diseases that can be combated with the fungicidal formulations according to the present invention diseases caused by Ascomycete fungi, such as Erysiphales as for example *Erysiphe cichoracearum* or *Uncinula necator*, and Dothideals as for example *Venturia inaequalis* or *Septoria tritici* (*Mycosphaerella gramini-cola*).

For a more clear understanding of the invention, specific examples thereof are set forth below.

The test results described below demonstrate the enhancement in fungicidal efficacy of triazolopyrimidines of formula I by the addition of adjuvants according to the invention.

EXAMPLE 1

Greenhouse Evaluations for Curative and Residual Fungicidal Activity

The formulated compound (see formulation below) was prepared as an aqueous suspension using concentrations of 100, 20 and 4 ppm active ingredient (a.i.) and was applied to greenhouse plants using a single-nozzle overhead rack sprayer at an application rate of 200 liter/ha. Within the 200 l/ha the compound was alternatively intank mixed with 1000 ppm of adjuvant(s) (as given in tale of results). In case two adjuvants were added to the compound, the concentration of each, adjuvant was 500 ppm.

Barley seedlings (var. 'Golden Promise') and wheat seedlings (var. 'Kanzler') were grown to the primary leaf stage (ca. 1 week old) in 6-cm-diameter pots in the greenhouse.

Plants for both curative and residual tests were sprayed at the same time with inoculations of the pathogens being done in different days.

For curative tests, barley and wheat plants were inoculated 2 days prior to compound treatment by dusting with conidia of *Blumeria* (*Erysiphe*) *graminis* f.sp. *hordei* or *B. graminis* f.sp. *tritici* to create powdery mildew diseases. Plants were kept in the greenhouse until treated. After treatment, the plants were returned to the greenhouse and kept there until powdery mildew disease symptoms/signs developed on untreated plants.

Plants were than evaluated for percent disease on the treated primary leaves. For curative rust tests, wheat plants were inoculated 2 days prior to compound treatment by spraying with a urediniospore suspension in 0.05% aqueous Tween 10 (1 mg spores per ml) of Puccinia recondita, kept in a moist infection chamber for one day then moved to the greenhouse until treated. After treatment the plants were kept in the greenhouse until disease symptoms/signs developed on a untreated plants. Plants were then evaluated for percent disease on the treated primary leaves.

For residual tests, plants were treated first and then kept for 4 days in the greenhouse before being inoculated with the pathogens as described for curative tests. Inoculated plants were kept in the greenhouse until disease symptoms/signs develop on untreated plants. Plants were the evaluated for percent disease on the treated primary leaves.

Disease control efficacy was calculated from the percent disease values using the following formula:

$$\% \text{ disease control} = 100 - \frac{\% \text{ infected leaf area in treated plants}}{\% \text{ infected leaf area in untreated plants}}$$

Table I gives the means of the efficacy (%control) of the three concentrations of compound IA used. This is accepted because the adjuvant concentrations were the same at all the compound a.i. concentrations used.

The composition of formulation R in Table I is

Formulation R: Suspension Concentrate (SC)

| Component | Amount [g/l] | Ingredient |
|---|---|---|
| active ingredient | 100.0 | Compound IA |
| dispersant | 20.0 | Atlas G5000[1] |
| dispersant | 10.0 | Synperonic A[1] |
| antifoam agent | 3.0 | Rhodorsil ® 426[2] |
| preservative | 2.0 | Proxel ® GXL[3] |
| structure agent | 3.0 | Rhodopol ® 23[2] |
| antifreeze agent | 50.0 | propylene glycol |
| water | to 1000 ml | |

[1]Uniqema, Everberg, Belgium
[2]Rhodia GmbH, Frankfurt, Germany
[3]Zeneca GmbH, Frankfurt, Germany

TABLE I

| | Mean % Control Over 3 Rates (100-20-4 ppm) of Compound 1A | | | | | |
|---|---|---|---|---|---|---|
| | WPM* | | WLR* | | BPM* | |
| Treatment | 2 Day Curative | 4 Day Residual | 2 Day Curative | 4 Day Residual | 2 Day Curative | 4 Day Residual |
| Formulation A | 16 | 42 | 48 | 10 | 21 | 14 |
| Formulation A & Pluarafac LF 300 (1000 ppm) | 49 | 40 | 69 | 28 | 69 | 30 |
| Formulation A & Lubrol 17A17 (1000 ppm) | 43 | 33 | 72 | 15 | 38 | 26 |
| Formulation A & Pluarafac LF 700 (500 ppm) + Lubrol 17A17 (500 ppm) | 42 | 40 | 79 | 33 | 38 | 28 |
| Formulation A & Pluarafac LF 300 (500 ppm) + Lubrol 17A17 (500 ppm) | 55 | 49 | 78 | 38 | 57 | 43 |
| Formulation A & Berol 381 (1000 ppm) | 52 | 47 | 72 | 23 | 54 | 38 |
| Formulation A & Ethimeen S 22 (1000 ppm) | 53 | 48 | 72 | 22 | 56 | 28 |
| Formulation A & Ceridust 9615 A | 29 | 45 | 62 | 27 | 35 | 32 |

*WPM = wheat powdery mildew; WLR = wheat leaf rust, BPM = barely powdery mildew

The invention claimed is:

1. An aqueous suspension concentrate (SC) comprising at least one triazolopyrimidine of formula I

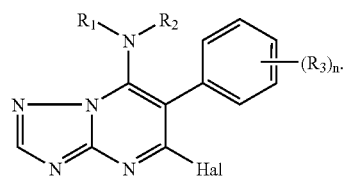

in which $R^1$ and $R^2$ independently denote hydxogen, or
(i) $C_1$–$C_{10}$-alkyl, $C_2$–$C_{10}$-alkenyl, $C_2$–$C_{10}$-alkynyl, or $C_4$–$C_{10}$-alkadienyl, $C_3$–$C_{10}$-cycloalkyl, phenyl, naphthyl, or 5- or 6-membered heterocyclyl, containing one to four nitrogen atoms or one to three nitrogen atoms and one sulfur or oxygen atom, or 5- or 6-membered heteroaryl, containing one to four nitrogen atoms or one to three nitrogen atoms and one sulfur or oxygen atom, or (ii) $R^1$ and $R^2$ together with the nitrogen atom to which they are bonded represent a 5- or 6-membered heterocyclic ring, containing one to four nitrogen atoms or one to three nitrogen atoms and one sulfur or oxygen atom, where $R^1$ and $R^2$ radicals of (i) and (ii) may be unsubstituted or may carry one to three groups $R^a$, $R^a$ is cyano, nitro, hydroxyl, $C_1$–$C_6$-alkyl, $C_1$–$C_6$-haloalkyl, $C_3$–$C_5$-cycloalkyl, $C_1$–$C_6$-alkoxy, $C_1$–$C_6$-haloalkoxy, $C_1$–$C_6$-alkylthio, $C_1$–$C_6$-alkylamino, di-$C_1$–$C_6$-alkylamino, $C_2$–$C_6$-alkenyl. $C_2$–$C_6$-alkenyloxy, $C_2$–$C_6$-alkynyl, $C_3$–$C_6$-alkynyloxy and $C_1$–$C_4$-alkylenedioxy;

$R^3$ represents halogen or $C_1$–$C_6$-alkyl or $C_1$–$C_6$alkoxy;

n represents an integer from 0 to 5; and

Hal represents halogens, together with one or more adjuvants selected from the group consisting of non-ionic water-soluble mixed polyalkoxylated aliphatic alcohol surfactants which is a random or block oligomer, both forms being represented by formula II

  (II)

wherein n is an integer from 8 to 18;

x is an integer from 3 to 10;

y is an integer from 1 to 3;

the adjuvant is present in an amount sufficient to provide a ratio of the compound of formula I to adjuvant at 100:75 to 100:100000 in the applied formulation.

2. The formulation according to claim 1 comprising an additional fungicidal compound.

3. The formulation according to claim 1, wherein the relative proportion of the triazolopyrimidine of formula I to the adjuvant is from 100:90 to 100:50000.

4. The formulation according to claim 1, wherein the relative proportion of the triazolopyrimidine of formula I to said adjuvant is from 100:125 to 100:5000.

5. A method for controlling phytopathogenic fungi, said method comprising applying the aqueous suspension concentrate of claim 1 to plants at a rate of 60 to 2000 ml/ha.

6. An aqueous suspension concentrate (SC) comprising at least one triazolopyrimidine of formula I

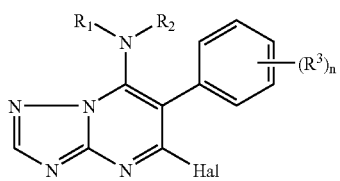  I in which $R^1$ and $R^2$ independently denote hydrogen, or (i) $C_3$–$C_{10}$-alkyl, $C_2$–$C_{10}$-alkynyl, $C_2$–$C_{10}$-alkynyl, or $C_4$–$C_{10}$alkadienyl, $C_3$–$C_{10}$-cycloalkyl, phenyl, naphthyl, or 5 or 6-membered heteroaryl, containing one to four nitrogen atoms or one to three nitrogen atoms and one sulfur or oxygen atom, or 5- or 6-membered heteroaryl, containing one to four nitrogen atoms or one to three nitrogen atoms and one sulfur or oxygen atom, or (ii) $R^1$ and $R^2$ together with the nitrogen atom to which they are bonded represent a 5 -or 6-membered heterocyclic ring, containing one to four nitrogen atoms or one to three nitrogen atoms and one sulfur or oxygen atom, where $R^1$ and $R^2$ radicals of (i) and (ii) may be unsubstituted or may carry one to three groups $R^a$, $R^a$ is cyano, nitro, hydroxyl, $C_1$–$C_6$-alkyl, $C_1$–$C_6$-haloalkyl, $C_3$–$C_6$-cycloakyl, $C_1$–$C_6$-alkoxy, $C_1$–$C_6$-haloalkoxy, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_2$–$C_6$-alkynyl, $C_3$–$C_6$-alkynyloxy and $C_1$–$C_6$-alkylenedioxy;

$R^3$ represents halogen or $C_1$–$C_6$-alkyl or $C_1$–$C_6$-alkoxy;

n represents an integer from 0 to 5; and

Hal represents halogen, together with a combination of (a) one or more adjuvants selected from the group consisting of non-ionic water-soluble mixed polyalkoxylated aliphatic alcohol surfactants which is a random or block oligomer, both forms being represented by formula II

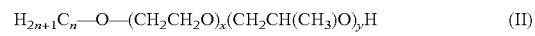  (II)

where in a is an integer from 8 to 18;

x is an integer from 3 to 10;

y is an integer from 1 to 3; and (b) one or more adjuvants selected from the group consisting of non-ionic water soluble ethoxylated aliphatic alcohol surfactants, wherein the adjuvants are present in an amount sufficient to provide a ratio of the compound of formula I to said combination at 100:75 to 100:100000 in the applied formulation.

7. The formulation according to claim 6 comprising an additional fungicidal compound.

8. The formulation according to claim 6 wherein the relative proportion of the triazolopyrimidine of formula I to said combination is from 100:90 to 100:50000.

9. The formulation according to claim 6, wherein the relative proportion of the triazolopyrimidine of formula I to said combination is tract 100:125 to 100:5000.

* * * * *

UNITED STATES PATENT AND TRADEMARK OFFICE
CERTIFICATE OF CORRECTION

PATENT NO.        : 7,176,209 B2
APPLICATION NO. : 10/362058
DATED              : February 13, 2007
INVENTOR(S)      : Aven et al.

Page 1 of 2

It is certified that error appears in the above-identified patent and that said Letters Patent is hereby corrected as shown below:

On the title page item (57) Line 1 of the Abstract:
"non/ionic water/soluble" should read --non-ionic water-soluble--

On the title page item (57) Line 2 of the Abstract:
"polyalkoxy–lated" should read --polyalkoxylated-- and
"non ionic" should read --non–ionic--

On the title page item (57) Lines 5 and 11 of the Abstract:
"triazolopzrimidines" should read, in each case, --triazolopyrimidines--

On the title page item (57) Line 12 of the Abstract:
"photopathogenic" should read --phytopathogenic--

On the title page item (57) Line 13 of the Abstract:

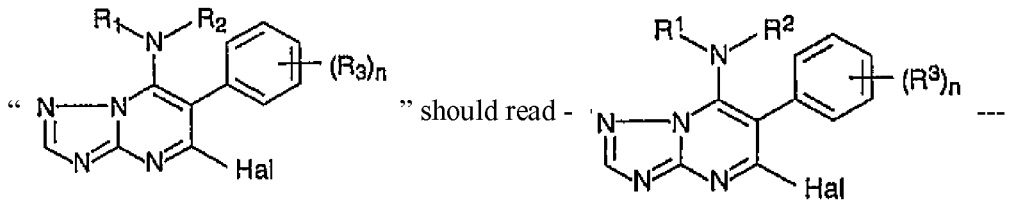

In Claim 1, col. 8 at indicated lines 45–50:

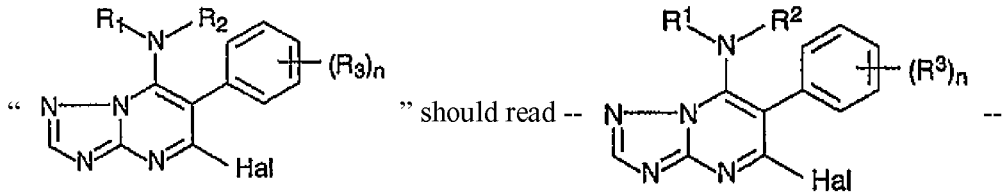

In Claim 1, col. 9, indicated line 7:
"$C_3$–$C_5$–cycloalkyl" should read --$C_3$–$C_6$–cycloalkyl--

In Claim 1, col. 9, indicated line 12:
"$C_1$–$C_6$alkoxy" should read --$C_1$–$C_6$–alkoxy--

In Claim 6, col. 9 at indicated line 50:

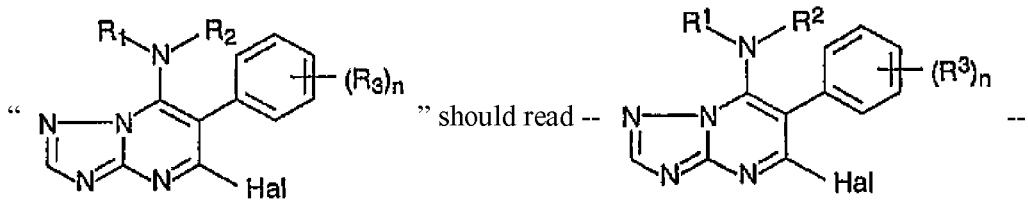

UNITED STATES PATENT AND TRADEMARK OFFICE
CERTIFICATE OF CORRECTION

PATENT NO. : 7,176,209 B2
APPLICATION NO. : 10/362058
DATED : February 13, 2007
INVENTOR(S) : Aven et al.

It is certified that error appears in the above-identified patent and that said Letters Patent is hereby corrected as shown below:

In Claim 6, col. 10, indicated line 3:
  "$C_3$–$C_{10}$–alkyl" should read --$C_1$–$C_{10}$–alkyl-- and
  "$C_2$–$C_{10}$–alkynyl, $C_2$–$C_{10}$–alkynyl" should read --$C_2$–$C_{10}$–alkenyl, $C_2$–$C_{10}$–alkynyl--
In Claim 6, col. 10, indicated line 6:
  "5 or 6–membered heteroaryl" should read --5– or 6–membered heterocyclyl"
In Claim 6, col 10, indicated line 13:
  "5 –or 6–membered" should read --5– or 6–membered--
In Claim 9, col. 10, indicated line 54:
  "tract" should read --from--

Signed and Sealed this

Thirty-first Day of July, 2007

JON W. DUDAS
*Director of the United States Patent and Trademark Office*